(12) United States Patent
Law et al.

(10) Patent No.: US 7,247,143 B2
(45) Date of Patent: Jul. 24, 2007

(54) BLADDER-BASED CUFF FOR MEASURING PHYSIOLOGICAL PARAMETERS AND METHOD OF MEASURING PHYSIOLOGICAL PARAMETERS USING SAME

(75) Inventors: Perry N. Law, Centerville, UT (US);
Douglas L. Cox, Morgan, UT (US);
David R. Miller, Morgan, UT (US);
David A. Bell, Farmington, UT (US)

(73) Assignee: Hema Metrics, Inc., Kaysville, UT (US)

( * ) Notice: Subject to any disclaimer, the term of this patent is extended or adjusted under 35 U.S.C. 154(b) by 83 days.

(21) Appl. No.: 10/695,441

(22) Filed: Oct. 29, 2003

(65) Prior Publication Data

US 2005/0096552 A1    May 5, 2005

(51) Int. Cl.
*A61B 5/02* (2006.01)
*A61B 17/00* (2006.01)

(52) U.S. Cl. ........................ 600/499; 606/202
(58) Field of Classification Search ................ 600/499; 606/202; 602/13
See application file for complete search history.

(56) References Cited

U.S. PATENT DOCUMENTS

| | | | |
|---|---|---|---|
| 3,482,565 A * | 12/1969 | Gowen ................... | 600/480 |
| 3,701,349 A * | 10/1972 | Larson ................... | 602/14 |
| 3,935,984 A * | 2/1976 | Lichowsky et al. ...... | 600/499 |
| 4,025,682 A | 5/1977 | Cieciuch et al. | |
| RE29,402 E * | 9/1977 | Shotwell ................ | 16/431 |
| 4,138,254 A | 2/1979 | Rogers | |
| 4,191,679 A | 3/1980 | Okita | |
| 4,202,347 A | 5/1980 | Sacks | |
| 4,256,094 A * | 3/1981 | Kapp et al. ............. | 601/152 |
| 4,331,155 A | 5/1982 | Sacks | |
| 4,726,382 A | 2/1988 | Boehmer et al. | |
| 4,747,415 A | 5/1988 | Lavoisier | |
| 4,865,038 A | 9/1989 | Rich et al. | |
| 5,025,793 A | 6/1991 | Richley et al. | |
| 5,218,966 A | 6/1993 | Yamasawa | |
| 5,423,322 A | 6/1995 | Clark | |
| 5,511,551 A * | 4/1996 | Sano et al. ............. | 600/499 |
| 5,676,140 A * | 10/1997 | Ukawa et al. ........... | 600/311 |
| 5,692,520 A | 12/1997 | Lavoisier | |
| 5,807,266 A * | 9/1998 | Itonaga et al. .......... | 600/499 |

(Continued)

*Primary Examiner*—Robert Nasser
(74) *Attorney, Agent, or Firm*—Jacobson Holman PLLC

(57) ABSTRACT

A cuff for measuring volume and change in volume of a body appendage includes a hollow, rigid tube having an inner surface; and a bladder having an inner surface and an outer surface, the ends of the bladder being sealed to the ends of the tube to create an enclosed internal volume between the inner surface of the bladder and the inner surface of the tube and an external volume defined by the outer surface of the bladder and surrounded by the internal volume, the bladder having a normal, relaxed state, in which the internal volume is filled with a fluid and a retracted state in which the fluid is evacuated from the internal volume. Two stiffener ribs placed on the inner surface of the bladder, parallel to each other and to the lengthwise axis of the tube at diametrically opposite positions. A plurality of emitters and detectors arranged in a linear array are embedded in one of the ribs, so as to emit and detect light through the bladder. A fluid port extending through the tube and communicating with the internal volume, through which the internal volume can be filled with or emptied of the fluid.

6 Claims, 1 Drawing Sheet

U.S. PATENT DOCUMENTS

| | | |
|---|---|---|
| 6,087,081 A | 7/2000 | Yamanouchi et al. |
| 6,173,196 B1 | 1/2001 | Delonzor et al. |
| 6,181,958 B1 | 1/2001 | Steuer et al. |
| 6,801,798 B2 * | 10/2004 | Geddes et al. .............. 600/323 |

* cited by examiner

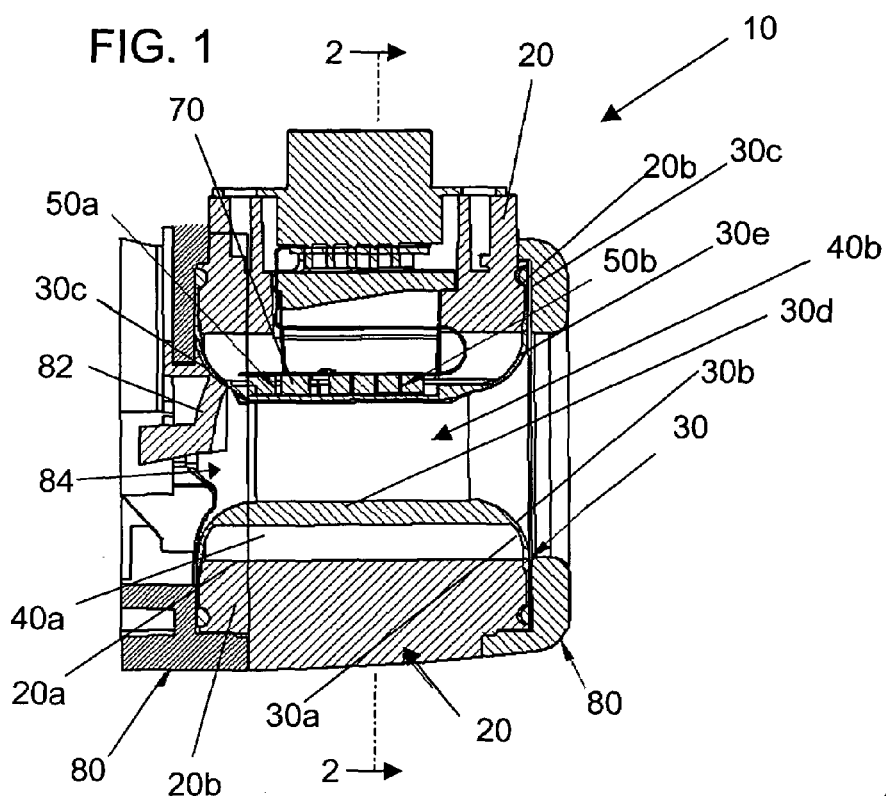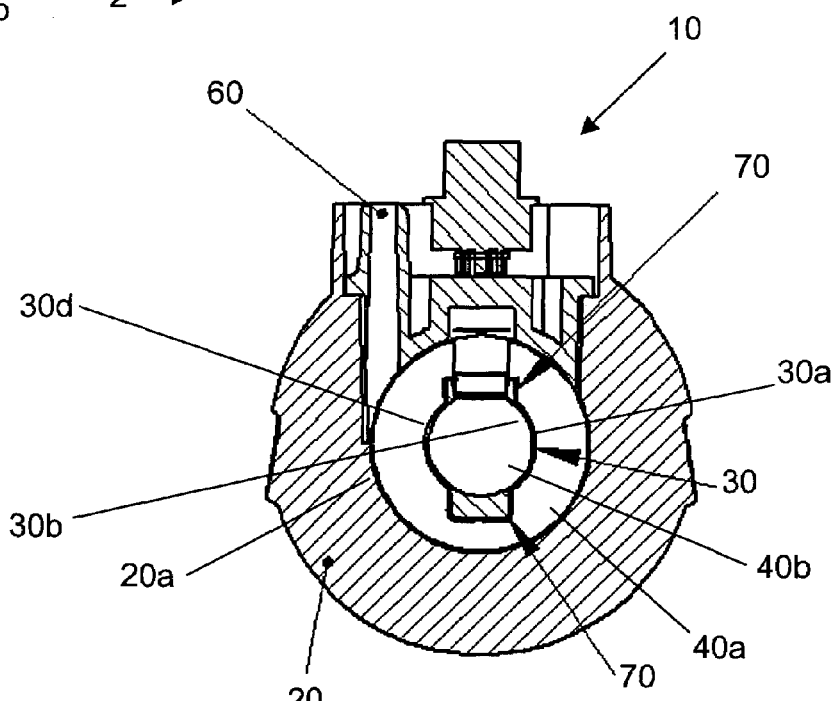

BLADDER-BASED CUFF FOR MEASURING PHYSIOLOGICAL PARAMETERS AND METHOD OF MEASURING PHYSIOLOGICAL PARAMETERS USING SAME

FIELD OF THE INVENTION

The invention relates to inflatable cuff devices. More specifically, it relates to inflatable cuff devices for measuring volume and/or the change in volume with respect to some physiological parameter of a body appendage, and a method of measuring physiological parameters using an inflatable cuff device.

BACKGROUND OF THE INVENTION

Inflatable cuff devices are used in a variety of applications to measure such parameters as volume, change in volume, pressure, response to pressure, occlusion, and response to occlusion. See, for example, U.S. Pat. Nos. 4,747,415 and 5,692,520 to Lavoisier. These measurements are used widely in, but not limited to, the medical community to assay physiological parameters. Examples of such physiological parameters are blood pressure, cardiac cycle (plythesmography), blood flow, and pulse rate, to name a few. In each case, a bladder-based cuff device is placed around or in contact with the object to be measured (usually a body appendage such as an arm or a fingertip) and a gas, generally air, is pumped into the bladder, causing the bladder to inflate and thus reduce the inner diameter of the cuff. It should be noted that media other than air can be used; however, alternative media such as liquids have the disadvantage of being essentially non-compressible. The reduction of the inner diameter of the cuff results in an excess of bladder material being compressed into the area where the cuff engages the object to be measured. This excess of material creates folds, bends, wrinkles, and voids at the cuff/object interface. Depending upon the nature of the measurement, these irregularities generally result in a source of measurement error.

Also, there is a need for a device that accurately measures both the volume and the change in volume of a body appendage as blood or other fluids (such as water) pulse in and out or as fluid accumulates to cause swelling. For a device in which measurements of additional physiological parameters are made using optical emitters and detectors, the device preferably also holds the emitters and detectors against the body appendage in a predictable manner, simultaneous with measuring the volume or the volume changes in the body appendage. In holding the components against the body appendage, the bladder must not allow any air gaps or incorrect alignment of the emitters or detectors. The bladder must also be able to conform to the many different profiles of body appendages, while still allowing for accurate volume and optical measurements.

The prior art includes many devices in which a bladder inflates against the finger. Examples of such prior art are disclosed in U.S. Pat. Nos. 4,202,347 and 4,331,155 to Sacks, U.S. Pat. No. 5,025,793 to Richley et al., and U.S. Pat. No. 5,218,966 to Yamasawa. In each case, as the bladder inflates against the finger, gaps are caused by the folding of the bladder material. In addition, the bladders do not conform in a predictable way to each of the different shapes of fingers. These variances cause any measurements made by the bladders to be unpredictable and prone to inaccuracies. Through experimentation, we have concluded that it is not possible to build a bladder that simply inflates from a static, un-inflated position to a variety of body appendage shapes and sizes without having gaps, folds, bends, or wrinkles. Thus, the prior art devices inherently introduce errors into the measurements.

It is to the solution of these and other problems that the present invention is directed.

BRIEF SUMMARY OF THE INVENTION

It is therefore a primary object of the present invention to provide a bladder-based cuff device for measuring physiological parameters of an appendage that conforms to any known shape and size of appendage without folds, bends, wrinkles, and voids at the cuff/appendage interface, so as to insure that the measurements are accurate.

It is another object of the present invention to provide a bladder-based cuff device that accurately measures both the volume and the change in volume of a body appendage as blood or other fluids (such as water) pulse in and out or as fluid accumulates to cause swelling.

It is still another object of the present invention to provide a bladder-based cuff device that conforms to any known body appendage shape and size without gaps and insures accurate and predictable placement of the emitters and detectors.

These and other objects of the present invention are achieved by the provision of a cuff for measuring physiological parameters of an appendage wherein the cuff includes a hollow, rigid tube having an inner surface and opposed ends; and a bladder having an inner surface, an outer surface, and opposed ends. The ends of the bladder are sealed to the ends of the tube to create an enclosed internal volume between the inner surface of the bladder and the inner surface of the tube and an external volume defined by the outer surface of the bladder and surrounded by the internal volume. The bladder has a normal, relaxed state, in which the internal volume is filled with a fluid and a retracted state in which the fluid is evacuated from the internal volume. Two stiffener ribs are placed on the inner surface of the bladder, parallel to each other and to the lengthwise axis of the tube at diametrically opposite positions. A plurality of emitters and detectors are arranged in a linear array are embedded in one of the ribs, so as to emit and detect light through the bladder. A fluid port extends through the tube and communicates with the internal volume, through which the internal volume can be filled with or emptied of the fluid.

In one aspect of the invention, the bladder is tubular in shape, with the ends of the bladder overlapping the ends of the tube, and wherein the thickness of the bladder is greater where the ends of the bladder overlap the ends of the tube.

In another aspect of the invention, the bladder, in its normal, relaxed state, has an inside diameter smaller than the diameter of the smallest of the type of appendage to be measured, and is made of a material, such as a thin wall rubber or a thin wall silicone rubber, that allows the inside diameter to stretch at least to the diameter of the largest of the type of appendage to be measured, and return back to its original size without deforming.

BRIEF DESCRIPTION OF THE DRAWINGS

FIG. 1 is a cross-sectional view of a bladder-based cuff in accordance with the present invention.

FIG. 2 is a cross-sectional view taken along line 2—2 of FIG. 1.

DETAILED DESCRIPTION OF THE INVENTION

Referring now to FIGS. 1 and 2, a bladder-based cuff 10 is shown in accordance with the present invention, comprising a hollow, rigid tube 20 having an inner surface 20a and opposed ends 20b, and a bladder 30 having an inner surface 30a, outer surface 30b, opposed ends 30c, and a center portion 30d between the opposed ends 30c, the ends 30c of the bladder 30 being sealed to the ends 20b of the tube 20 to create an enclosed internal volume 40a between the inner surface 30a of the bladder 30 and the inner surface 20a of the tube 20 and an open external volume 40b defined by the outer surface 30a of the bladder 30 and surrounded by the enclosed internal volume 40a. Preferably, the bladder 30 and the enclosed internal volume 40a are both tubular in shape, while the open external volume 40b is cylindrical, with the bladder 30, the enclosed internal volume 40a, and the open external volume 40b all having a common longitudinal axis that is collinear with the longitudinal axis of the tube 20.

The bladder 30 has a normal, relaxed state, in which the enclosed internal volume 40a is filled with a fluid, preferably air or another gas, and a retracted state, in which the fluid is evacuated from the internal volume 40a. In its relaxed state, the bladder 30 does not provide sufficient room for an appendage to be inserted into the external volume 40b; while in its retracted state, the bladder 30 does provide sufficient room for the appendage to be inserted into the external volume 40b. The appendage can be a finger (more specifically, a fingertip), an arm, or any other appendage having one or more physiological parameters normally measured by an inflatable cuff device.

A plurality of emitters 50a and detectors 50b are positioned within the interior of the tube 20, preferably inside the enclosed internal volume 40a, as discussed in greater detail hereinafter. Preferably, the emitters 50a and detectors 50b are positioned in a linear fashion parallel to the longitudinal axis of the tube 20, with the emitters 50a being side-by-side and the detectors 50b being side-by-side. In the embodiment shown in FIGS. 1 and 2, there are two emitters 50a and four detectors 50b. The emitters 50a may generate and emit either monochromatic light or multi-wavelength light, and each emitter 50a can include a variety of different types of light sources, including multiple discrete LEDs, multiple discrete laser diodes, and multiple emitting sources combined and coupled into multi-mode fiber optics, as examples. The number of emitters 50a, or more specifically, the number of wavelengths employed by the cuff 10, is governed by the number of parameters being measured other than volume or change in volume, as a different wavelength is required for each parameter. The number of detectors 50b is determined by the need for spatial differentiation. The factors governing the number of emitters 50a and detectors 50b are described in U.S. Pat. No. 6,181,958, which is incorporated herein by reference in its entirety.

A fluid port 60 extends through the tube 20 and communicates with the enclosed internal volume 40a, by which the internal volume 40a can be filled with or emptied of the fluid. The port 60 is attachable to means (not shown) for emptying fluid from the internal volume 40a and filling it with the fluid. This means can comprise a manifold connected to the fluid port 60 via a valve in the manifold and a pump to move the fluid into and out of the manifold, a syringe and a tube connecting the syringe to the fluid port 60, or any other mechanism designed to move fluids of any type. To allow the appendage to be inserted into the external volume 40b, the mechanism draws the fluid from the enclosed internal volume 40a, causing the bladder 30 to assume its retracted state (thus minimizing the enclosed internal 40a and maximizing the external volume 40b). Once the appendage has been placed into the external volume 40b, the mechanism releases the fluid back into the enclosed internal volume 40a so that the bladder 30 assumes a state in which it conforms to the contours of the appendage.

In order for the bladder 30 to conform to any shape of appendage, without gaps, it is necessary for the bladder 30, in its normal, relaxed state, to have an inside diameter smaller than the smallest of the type of appendage to be measured. To achieve this goal, the bladder 30 is made of a material that allows the inside diameter to stretch at least to the diameter of the largest of the type of appendage to be measured. When the fluid is evacuated from the enclosed internal volume 40a, a vacuum is created and the bladder 30 stretches, causing the diameters of the bladder 30 and the external volume 40b to increase until the bladder 30 conforms to the inner surface 20a of the tube 20, thus becoming larger than the largest of the type of appendage to be tested. When the fluid is returned to the enclosed internal volume 40a and the vacuum is released with an appendage inside the external volume 40b, the bladder 30 attempts to retract to its natural state and conforms to the appendage without any wrinkles or gaps.

The selection of the bladder material is very important. The material must be very soft and elastic, and must be able to stretch approximately two to three times its original diameter and return back to the starting size without deforming. In addition, the bladder material must be sufficiently impermeable to the fluid so as to minimize leakage, regardless of the amount the bladder 30 is stretched. The bladder material also must be of a type that can achieve a stable state with respect to its elasticity after it has been stretched. Due to these considerations, materials that are suitable for the bladder 30 include, but are not limited to, a rubber or a silicone rubber.

In addition, for practical purposes, the vacuum necessary to stretch the bladder 30 must be kept low to minimize the amount of force necessary to expand the bladder 30 so as to conform to the inner surface 20a. If the bladder 30 is made of a rubber or a silicone rubber material, then to meet the requirement that the bladder 30 be able to stretch to approximately two to three times its original diameter using a low vacuum, the bladder 30 must have a thin wall. However, the requirement of a thin wall raises another consideration. Thin wall rubbers and silicone rubbers are permeable. Because in some appendages, particularly a finger, the volume change is very, very small as blood or other fluids pulse in and out or as fluid accumulates to cause swelling, the change in pressure is also very small. As a result, when the change in pressure due to the pulsing or swelling of the body appendage is measured, it is also possible to measure the pressure loss in the bladder 30 due to the loss of fluid due to leakage through the wall of the bladder 30. A thin wall, between 0.012 inch and 0.016 inch thick, allows for the required amount of stretch while minimizing both fluid leakage and the force required to pull the bladder 30 against the surrounding inner surface 20a of the tube 20.

With a thin material of the specified thickness, it is necessary to provide a material having a high tear strength (for silicone rubber, for example, about 125 lb/in.), so that the bladder 30 will not be damaged in use as a result of being snagged by a fingernail or rough, course skin.

The exact shape of the bladder 30 is also very important. In early testing we found that when a vacuum is created behind a simple tubular bladder, the ends of the bladder always retracted first. This prevented the bladder from retracting with a smooth surface at the center section where the appendage is placed. Instead, there would be a fold in the center section that would prevent the bladder from conforming to the body appendage. The present invention employs a combination of features to overcome this problem.

First, two stiffener ribs 70 are placed on the inner surface 30a of the bladder 30, parallel to each other and to the longitudinal axis of the tube 20 at diametrically opposite positions, to reduce buckling. The ribs 70 must be wide enough and thick enough to provide the stability needed, but they must be narrow enough so that the stretch area of the bladder 30 is not reduced to the point that the force necessary to cause the bladder 30 to retract against the inner surface 20a of the tube 20 is too great. In addition, the height of the stiffener ribs 70 must be minimized in order to maximize the retracted diameter of the bladder 30 for a given diameter of the inner surface 20a, and to allow for the insertion of the largest appendage of the type being targeted. The exact dimensions of the ribs 70 will therefore depend on the relative size of the bladder 30, the desired maximum retraction diameter of the inner surface 20a, and the desired force required to retract the bladder 30.

Second, we have discovered that the shape and thickness of the bladder 30 at the transition region 30e between the ends 30c and the center portion 30d is critical for proper bladder retraction. There must be a relatively gradual transition from the ends 30c of the bladder 30 to the center portion 30d. Furthermore, the bladder thickness must be about 30% greater within the transition region 30e as compared to the thickness of the center portion 30d, to increase the stiffness of the bladder 30 and decrease transition buckling upon bladder retraction. We have also found that the ends 30c of the bladder 30 must overlap the ends 20b of the tube 20 by about 30% to achieve the desired stiffness, that is, to decrease buckling at the transition region 30e between the ends 30c and the center portion 30d upon retraction of the bladder 30.

The thickness of the bladder 30 also is greater (about 70% thicker) where the ends 30c of the bladder 30 overlap the ends 20b of the tube 20. End caps 80 are provided at the ends 20b of the tube 20 to cover the ends 30c of the bladder 30 where they overlap the ends 20b of the tube 20.

In an embodiment in which the cuff 10 is used to make one or more optical measurements in addition to the volume measurement, the emitters 50a and detectors 50b must be attached to the cuff 10 such that they are held firmly against the appendage without allowing an air gap or creating a ridge line that pushes against the appendage. The manner in which the emitters 50a and detectors 50b are attached must be such that they are secure and cannot separate from the bladder 30. In order to make a smooth surface against the appendage with no ridge lines, the emitters 50a and detectors 50b are placed on the inner surface 30a of the bladder 30, and the emitters 50a and detectors 50b respectively emit and detect light through the bladder 30. In particular, one of the stiffener ribs 70 includes a receiving cavity 72 dimensioned to accommodate the emitters 50a and detectors 50b so that they are always placed in a consistent manner. Once the emitters 50a and detectors 50b have been placed within the receiving cavity 72, an adhesive specifically made for the bladder material is applied as an overlay to attach the emitters 50a and detectors 50b to the bladder 30. The application and adhesion methods are critical to ensure that no air or excess glue remain between the surface of the emitters 50a or detectors 50b and the inner bladder surface 30a.

To ensure consistent optical and pressure measurements, the placement of the appendage within the external volume 40b must be consistent with respect to the emitters 50a and detectors 50b. Furthermore, the placement of the appendage must be in a manner to minimize any anatomical or physiological disturbances of the appendage. In the embodiment in which the cuff 10 is used, a sensitive capacitive touch sensor is used as a finger-stop 82 to ensure proper finger positioning within the external volume 40b and to minimize blanching. In addition, a gap 84 between the upper surface of the finger sensor and the corresponding end cap 80 accommodates a large range of finger nail sizes.

Placing the emitters 50a and detectors 50b on the inside surface of the bladder 30 raises another consideration that must be addressed. Light passing though the bladder 30 from the emitters 50a to the detectors 50b without passing though the appendage is called light piping, and is an error source that must be eliminated. To eliminate light piping, the bladder material is tinted with appropriate pigments selected to absorb the specific wavelengths of light employed, effectively damping the light piping signal. The nature of the tint must be such that at the wavelength of light of interest is heavily attenuated for the minimum separation distance of the source and detector. In a preferred embodiment of the bladder-based cuff 10, the minimum distance is the distance between the illuminating source (the emitters 50a) and the closest of the detectors 50b. This distance is generally no less than 4–5 mm. The attenuation should be such to decrease the intensity of piped light to below that of the governing signal-to-noise ratio ("SNR") of the detecting channels. That is, the voltage induced within the detectors 50b due to light piping should be less than the inherit noise of the electronics and other sources.

In addition to damping the light piping signal, it is desirable to allow as much light as possible to pass from the emitters 50a through the bladder 30 and into the appendage. As a result, the amount and combination of pigment in the bladder 30 is critical. Acceptable tinting is therefore a function of the initial electromagnetic intensity, wavelength, bladder thickness, and distance to the nearest detector 50b. An acceptable tinting has been accomplished for wavelengths between 600 and 900 nm at a concentration of 100 parts adhesive to 22 and 20 parts black and blue silicone pigments, respectively.

For the most accurate optical measurements, illumination and detection surfaces should not produce inhomogeneities in the finger or tissue beds. The soft and pliable surface of the bladder 30 offers an ideal tissue-to-optical interface by supplying a continuous engagement surface for the finger and measuring system. To maintain the best engagement surface possible, the placement of the electro-optical components (that is, the emitters 50a and detectors 50b) is therefore on the side of the bladder 30 opposite the finger placement. However, this opposite placement of the emitters 50a and detectors 50b relative to the finger necessitates the transmission of the light through the bladder 30 twice, once for illumination and once for detection. Thus, in addition to the optimization of tinting substance(s) and concentration (s), it is also necessary to optimize the thickness of the bladder 30 between the finger and the illumination source (that is, the emitters 50a). In other words, the bladder material must be optimized to allow sufficient light to pass therethrough into and out of the tissue to: (1) properly illuminate the tissue and (2) properly detect the light backscattered from the tissue.

Building on the need both to attenuate unintentional traverse piping of light between the illuminating source (emitters 50a) and the detectors 50b, specifically selected tinting substances employed within the bladder material can provide wavelength selectivity. For example, any ambient or stray light that couples through finger or tissue bed into the detectors 50b that does not originate from the designated illumination source(s) (emitters 50a), results in measurement errors or uncertainties. Accordingly, the selection and concentration of tinting substances should provide wide-spectrum attenuation to minimize non-specific light detection. Conversely, the tinting selection and concentration may be such that a specific wavelength is selected or allowed to pass through the bladder 30 without significant attenuation, while all others are inhibited. Carefully considering the characteristics of the bladder material, the geometric spacing of the optical components, and the wavelengths of the emitters 50a, the tinting and design of the bladder 30 can be optimized to meet a wide variety of light filtering needs. These filtering needs can include, but are not limited to, high-pass, low-pass, and notch-filter configurations.

To accommodate appendages other than fingers and finger tips, it is only necessary to modify the size of the above-described cuff 10, thus maintaining its functionality.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

We claim:

1. A cuff for measuring physiological parameters of an appendage, comprising:
   a hollow, rigid tube having an inner surface and opposed ends; and
   a bladder having an inner surface, an outer surface, and opposed ends, the ends of the bladder being sealed to the ends of the tube to create an enclosed internal volume between the inner surface of the bladder and the inner surface of the tube and an external volume defined by the outer surface of the bladder and surrounded by the internal volume, the bladder having a normal, relaxed state, in which the internal volume is filled with a fluid and a retracted state in which the fluid is evacuated from the internal volume,
   wherein the bladder is tubular in shape, and wherein the ends of the bladder overlap the ends of the tube, and wherein the thickness of the bladder is greater where the ends of the bladder overlap the ends of the tube.

2. The cuff of claim 1, wherein the bladder has a center portion between the ends and a transition region between the ends and the center portion, and wherein the thickness of the bladder is greater at the transition region.

3. A cuff for measuring physiological parameters of an appendage, comprising:
   a hollow, rigid tube having an inner surface and opposed ends;
   a bladder having an inner surface, an outer surface, and opposed ends, the ends of the bladder being sealed to the ends of the tube to create an enclosed internal volume between the inner surface of the bladder and the inner surface of the tube and an external volume defined by the outer surface of the bladder and surrounded by the internal volume, the bladder having a normal, relaxed state, in which the internal volume is filled with a fluid and a retracted state in which the fluid is evacuated from the internal volume; and
   two stiffener ribs placed on the inner surface of the bladder, parallel to each other and parallel to the longitudinal axis of the tube at diametrically opposite positions.

4. The cuff of claim 3, further comprising a plurality of emitters and detectors positioned in the enclosed internal volume.

5. The cuff of claim 4, wherein the emitters and detectors are embedded in one of the stiffener ribs.

6. A cuff for measuring physiological parameters of an appendage, comprising:
   a hollow, rigid tube having an inner surface and opposed ends;
   a bladder having an inner surface, an outer surface, and opposed ends, the ends of the bladder being sealed to the ends of the tube to create an enclosed internal volume between the inner surface of the bladder and the inner surface of the tube and an external volume defined by the outer surface of the bladder and surrounded by the internal volume, the bladder having a normal, relaxed state, in which the internal volume is filled with a fluid and a retracted state in which the fluid is evacuated from the internal volume;
   a plurality of emitters and detectors positioned in the enclosed internal volume, wherein the emitters and detectors are placed on the inner surface of the bladder, and the emitters and detectors respectively emit and detect light through the bladder; and
   a stiffener rib placed on the inner surface of the bladder, wherein the emitters and detectors are embedded in the stiffener rib.

* * * * *